United States Patent
Foster et al.

(10) Patent No.: US 9,504,822 B2
(45) Date of Patent: *Nov. 29, 2016

(54) INDUCTIVE ELEMENT FOR PROVIDING MRI COMPATIBILITY IN AN IMPLANTABLE MEDICAL DEVICE LEAD

(71) Applicant: Cardiac Pacemakers, Inc., St. Paul, MN (US)

(72) Inventors: Arthur J. Foster, Blaine, MN (US); Linda L. Evert, Circle Pines, MN (US); Joel P. Grover, St. Paul, MN (US); Jason T. Lenz, Maplewood, MN (US); Brendan E. Koop, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1 day.

This patent is subject to a terminal disclaimer.

(21) Appl. No.: 14/658,234

(22) Filed: Mar. 15, 2015

(65) Prior Publication Data
US 2015/0182744 A1 Jul. 2, 2015

Related U.S. Application Data

(63) Continuation of application No. 14/056,746, filed on Oct. 17, 2013, now Pat. No. 8,983,623.

(60) Provisional application No. 61/715,627, filed on Oct. 18, 2012.

(51) Int. Cl.
*A61N 1/00* (2006.01)
*A61N 1/08* (2006.01)
*A61N 1/05* (2006.01)

(52) U.S. Cl.
CPC . *A61N 1/08* (2013.01); *A61N 1/05* (2013.01); *A61N 1/0587* (2013.01); *A61N 2001/086* (2013.01)

(58) Field of Classification Search
CPC ..................... A61N 1/3718; A61N 2001/086
USPC ..................... 607/37, 63, 115, 116
See application file for complete search history.

(56) References Cited

U.S. PATENT DOCUMENTS 3,614,692 A   10/1971   Rozelle et al.
4,131,759 A   12/1978   Felkel
(Continued)

FOREIGN PATENT DOCUMENTS

CN   17652510 A   4/2006
CN    1905789 A   1/2007
(Continued)

OTHER PUBLICATIONS

International Search Report and Written Opinion issued in PCT/US2013/065517, mailed Dec. 20, 2013, 11 pgs.
(Continued)

*Primary Examiner* — Allen Porter, Jr.
(74) *Attorney, Agent, or Firm* — Faegre Baker Daniels LLP (57) ABSTRACT

A system includes a medical device lead including a connector at a proximal end of the lead, a conductor electrically connected to the connector at a proximal end of the conductor, and at least one electrode coupled to a distal end of the conductor. The system further includes a device securable to the proximal end of the lead including an inductive element. The device includes a port configured to receive the connector and position the inductive element around at least a portion of the connector.

20 Claims, 5 Drawing Sheets

(56) References Cited

U.S. PATENT DOCUMENTS

| | | |
|---|---|---|
| 4,135,518 A | 1/1979 | Dutcher |
| 4,146,036 A | 3/1979 | Dutcher et al. |
| 4,209,019 A | 6/1980 | Dutcher et al. |
| 4,253,462 A | 3/1981 | Dutcher et al. |
| 4,350,169 A | 9/1982 | Dutcher et al. |
| 4,381,013 A | 4/1983 | Dutcher |
| 4,404,125 A | 9/1983 | Abolins et al. |
| 4,437,474 A | 3/1984 | Peers-Trevarton |
| 4,484,586 A | 11/1984 | McMickle et al. |
| 4,493,329 A | 1/1985 | Crawford et al. |
| 4,574,800 A | 3/1986 | Peers-Trevarton |
| 4,643,202 A | 2/1987 | Roche |
| 4,643,203 A | 2/1987 | Labbe |
| 4,649,938 A | 3/1987 | McArthur |
| 4,869,970 A | 9/1989 | Gulla et al. |
| 5,002,067 A | 3/1991 | Berthelsen et al. |
| 5,003,975 A | 4/1991 | Hafelfinger et al. |
| 5,020,545 A | 6/1991 | Soukup |
| 5,056,516 A | 10/1991 | Spehr |
| 5,074,313 A | 12/1991 | Dahl et al. |
| 5,144,960 A | 9/1992 | Mehra et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camps et al. |
| 5,243,911 A | 9/1993 | Dow et al. |
| 5,246,014 A | 9/1993 | Williams et al. |
| 5,259,395 A | 11/1993 | Li |
| 5,300,108 A | 4/1994 | Rebell et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,542,173 A | 8/1996 | Mar et al. |
| 5,542,174 A | 8/1996 | Chiu |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,649,974 A | 7/1997 | Nelson et al. |
| 5,658,709 A | 8/1997 | Layman et al. |
| 5,676,694 A | 10/1997 | Boser et al. |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Yung-Hui Chien et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,701,191 B2 | 3/2004 | Schell |
| 6,721,600 B2 | 4/2004 | Jorgenson et al. |
| 6,721,604 B1 | 4/2004 | Robinson et al. |
| 6,813,251 B1 | 11/2004 | Garney et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,909,256 B2 | 6/2005 | Wang |
| 6,920,361 B2 | 7/2005 | Williams |
| 6,925,334 B1 | 8/2005 | Salys |
| 6,944,489 B2 | 9/2005 | Zeijlemaker et al. |
| 6,949,929 B2 | 9/2005 | Gray et al. |
| 6,978,185 B2 | 12/2005 | Osypka |
| 6,985,755 B2 | 1/2006 | Cadieux et al. |
| 6,985,775 B2 | 1/2006 | Reinke et al. |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Dublin et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,180,688 B2 | 2/2007 | Kikuchi |
| 7,205,768 B2 | 4/2007 | Schulz et al. |
| 7,239,916 B2 | 7/2007 | Thompson et al. |
| 7,242,987 B2 | 7/2007 | Holleman et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,584,005 B1 | 9/2009 | Jain |
| 7,610,101 B2 | 10/2009 | Wedan et al. |

(56) References Cited

U.S. PATENT DOCUMENTS

| | | |
|---|---|---|
| 7,630,761 B2 | 12/2009 | Salo et al. |
| 7,689,291 B2 | 3/2010 | Polkinghorne et al. |
| 7,765,005 B2 | 7/2010 | Stevenson |
| 7,853,332 B2 | 12/2010 | Olsen et al. |
| 7,877,150 B2 | 1/2011 | Hoegh et al. |
| 7,912,552 B2 | 3/2011 | Przybyszewski |
| 7,917,213 B2 | 3/2011 | Bulkes et al. |
| 7,933,662 B2 | 4/2011 | Marshall et al. |
| 7,953,499 B2 | 5/2011 | Knapp et al. |
| 7,986,999 B2 | 7/2011 | Wedan et al. |
| 7,991,484 B1 | 8/2011 | Sengupta et al. |
| 8,000,801 B2 | 8/2011 | Stevenson et al. |
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,200,342 B2 | 6/2012 | Stevenson et al. |
| 8,214,055 B2 | 7/2012 | Erickson |
| 8,244,346 B2 | 8/2012 | Foster et al. |
| 8,255,055 B2 | 8/2012 | Ameri |
| 8,306,630 B2 | 11/2012 | Stubbs et al. |
| 8,315,715 B2 | 11/2012 | Erickson |
| 8,332,025 B2 | 12/2012 | Perry et al. |
| 8,335,572 B2 | 12/2012 | Ameri |
| 8,369,964 B2 | 2/2013 | Ameri |
| 8,391,994 B2 | 3/2013 | Foster et al. |
| 8,401,671 B2 | 3/2013 | Wedan et al. |
| 8,406,895 B2 | 3/2013 | Erbstoeszer et al. |
| 8,543,209 B2 | 9/2013 | Tyers et al. |
| 8,543,218 B2 | 9/2013 | Erickson |
| 8,666,508 B2 | 3/2014 | Foster et al. |
| 8,666,512 B2 | 3/2014 | Walker et al. |
| 8,670,828 B2 | 3/2014 | Hall et al. |
| 8,670,840 B2 | 3/2014 | Wedan et al. |
| 8,676,344 B2 | 3/2014 | Desai et al. |
| 8,676,351 B2 | 3/2014 | Foster et al. |
| 8,682,451 B2 | 3/2014 | Wengreen et al. |
| 8,688,236 B2 | 4/2014 | Foster |
| 8,731,685 B2 | 5/2014 | Ameri |
| 8,744,600 B2 | 6/2014 | Perrey et al. |
| 8,798,767 B2 | 8/2014 | Foster et al. |
| 8,825,179 B2 | 9/2014 | Walker et al. |
| 8,825,181 B2 | 9/2014 | Foster et al. |
| 8,954,168 B2 | 2/2015 | Foster |
| 8,983,623 B2 | 3/2015 | Foster et al. |
| 9,050,457 B2 | 6/2015 | Foster et al. |
| 9,199,077 B2 | 12/2015 | Foster et al. |
| 9,203,648 B2 | 12/2015 | Shraim et al. |
| 9,254,380 B2 | 2/2016 | Ameri et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1 | 5/2004 | Gardeski et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0227398 A1 | 10/2005 | Anderson et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2007/0255378 A1 | 11/2007 | Polkinghorne et al. |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1 | 5/2008 | Geistert |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |

(56) References Cited

U.S. PATENT DOCUMENTS

| | | |
|---|---|---|
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0198314 A1 | 8/2009 | Foster et al. |
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0049290 A1 | 2/2010 | Min et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0234929 A1 | 9/2010 | Scheuermann |
| 2010/0249892 A1 | 9/2010 | Bulkes et al. |
| 2010/0292744 A1 | 11/2010 | Hill et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0101558 A1 | 4/2012 | Kampa et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0232609 A1 | 9/2012 | Tyers et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2013/0282093 A1 | 10/2013 | Walker et al. |
| 2013/0325093 A1 | 12/2013 | Foster |
| 2014/0067030 A1 | 3/2014 | Walker et al. |
| 2014/0114383 A1 | 4/2014 | Foster et al. |
| 2014/0155972 A1 | 6/2014 | Foster et al. |
| 2014/0324139 A1 | 10/2014 | Foster et al. |
| 2015/0105846 A1 | 4/2015 | Foster |
| 2015/0238756 A1 | 8/2015 | Ameri et al. |

FOREIGN PATENT DOCUMENTS

| | | |
|---|---|---|
| CN | 101039619 A | 9/2007 |
| CN | 101553165 B | 10/2009 |
| CN | 102186534 A | 9/2011 |
| CN | 102209575 A | 10/2011 |
| CN | 104736196 A | 6/2015 |
| EP | 0897997 B1 | 2/2003 |
| EP | 1594564 A1 | 11/2005 |
| EP | 1852810 B1 | 11/2007 |
| EP | 2445577 B1 | 5/2012 |
| EP | 2227289 B1 | 7/2015 |
| EP | 2890446 A1 | 7/2015 |
| JP | H0747139 A | 2/1995 |
| JP | 2001522631 A | 11/2001 |
| JP | 2004511293 A | 4/2004 |
| JP | 2004141679 A | 5/2004 |
| JP | 2005501673 A | 1/2005 |
| JP | 2005515852 A | 6/2005 |
| JP | 2005515854 A | 6/2005 |
| JP | 2005522301 A1 | 7/2005 |
| JP | 2007520254 A | 7/2007 |
| JP | 2011504405 A | 2/2011 |
| JP | 2011509813 A | 3/2011 |
| JP | 2015520007 A | 7/2015 |
| WO | WO9606655 A1 | 3/1996 |
| WO | WO9923958 A1 | 5/1999 |
| WO | WO0232325 A1 | 4/2002 |
| WO | WO03063946 A2 | 8/2003 |
| WO | WO03063953 A2 | 8/2003 |
| WO | WO03089045 A2 | 10/2003 |
| WO | WO2004073791 A1 | 9/2004 |
| WO | WO2005030322 A1 | 4/2005 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO2009137186 A1 | 11/2009 |
| WO | WO20100078552 A1 | 7/2010 |
| WO | 2011081713 A1 | 7/2011 |
| WO | 2012038378 A1 | 3/2012 |
| WO | 2015130753 A1 | 9/2015 |

OTHER PUBLICATIONS

"High Voltage Engineering and Testing, 2nd Edition", edited by Hugh M. Ryan, Institution of Engineering and Technology, 2001, 15 pages.

Avalanche Breakdown, Wikipedia Article, captured Apr. 6, 2010, [http://en.wikipedia.org/wiki/Avalanche_breakdown].

Basso, Christophe, "SPICE Model Simulates Spark-Gap Arrestor", Electronics Design, Strategy, and News (EDN), Jul. 3, 1997, 4 pages.

Citel Inc., Data Sheet, BH Series 2 Electrode Miniature Gas Discharge Tube Surge Arrester—8mm, May 14, 2009, 2 pages.

File History for U.S. Appl. No. 11/015,807, filed Dec. 17, 2004 to Cooke, Daniel J. et al.

Gray, Robert W. et al., "Simple design changes to wires to substantially reduce MRI-induced heating at 1.5 T: implications for implanted leads", Magnetic Resonance Imaging 23 (2005) 887-891.

Hayes, David L., Chapter 4, "Generator and Lead Selection" from book entitled "Cardiac Pacing and Defribrillation A Clinical Approach", John Wiley & Sons, (C) 2000 Mayo Foundation, p. 129-157.

International Search Report and Written Opinion issued in PCT/US2008/085518 on Oct. 29, 2009, 15 pages.

International Search Report and Written Opinion issued in PCT/US2009/032838, mailed May 4, 2009, 14 pages.

International Search Report and Written Opinion issued in PCT/US2009/038629, mailed Jun. 29, 2009, 11 pages.

International Search Report and Written Opinion issued in PCT/US2009/056843, mailed Dec. 29, 2009, 13 pages International Search Report and Written Opinion issued in PCT/US2010/024062, mailed Sep. 27, 2010.

(56) References Cited

OTHER PUBLICATIONS

International Search Report and Written Opinion issued in PCT/US2010/033686 on Aug. 10, 2010, 12 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2011/052541, dated Mar. 9, 2012, 22 pages.
International Search Report and Written Opinion issued in PCT/US2012/055673, mailed Dec. 13, 2012, 10 pages.
International Search Report and Written Opinion issued in PCT/US2013/037432, mailed Nov. 19, 2013, 17 pages.
International Search Report and Written Opinion issued in PCT/US2013/057732, mailed Dec. 13, 2013, 11 pages.
Invitation to Pay Additional Fees and Partial Search Report, dated Aug. 17, 2009, issued in PCT/US2008/085533, 6 pages.
Invitaton to Pay Additonal Fees and Partal Seach Report, issued in PCT/US2010024062, mailed May 7, 2010.
Partial International Search Report issued in PCT/US2011/052541, mailed Dec. 6, 2011, 4 pages.
Partial International Search Report issued in PCT/US2013/013432, mailed Jul. 17, 2013, 6 pages.
Partial International Search Report issued in PCT/US2013/037432, mailed Jul. 17, 2013, 6 pages.
Static Spark Gap Analysis, captured Dec. 24, 2002, [http://www.richieburnett.co.uk/static.html].
Third Party Submission Under 37 CFR 1.290 filed in U.S. Appl. No. 14/056,746 on May 20, 2014, 13 pages.
International Preliminary Examination Report issued in PCT/US2013/065517, completed Apr. 21, 2015, 8 pages.
International Search Report and Written Opinion issued in PCT/US2015/017473, mailed May 20, 2015, 10 pages.

FIG. 5

INDUCTIVE ELEMENT FOR PROVIDING MRI COMPATIBILITY IN AN IMPLANTABLE MEDICAL DEVICE LEAD

CROSS-REFERENCE TO RELATED APPLICATION

This application is a continuation of U.S. application Ser. No. 14/056,746, filed Oct. 17, 2013, which claims the benefit of Provisional Application No. 61/715,627, filed Oct. 18, 2012, which are incorporated herein by reference in their entirety.

TECHNICAL FIELD

The present invention relates to implantable medical devices. More particularly, the present invention relates to an inductive element configured to associate with an implantable medical device to reduce MRI-induced currents in the implantable medical device.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas (T). During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic fields produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Discussed herein are various embodiments of an inductive element configured to associate with an implantable medical device lead to make the implantable medical device lead magnetic resonance (MR) conditional, as well as implantable medical device leads associated with such inductive elements.

In Example 1, a system includes a medical device lead including a connector at a proximal end of the lead, a conductor electrically connected to the connector at a proximal end of the conductor, and at least one electrode coupled to a distal end of the conductor. The system further includes a device securable to the proximal end of the lead including an inductive element. The device includes a port configured to receive the connector and position the inductive element around at least a portion of the connector.

In Example 2, the system according to Example 1, wherein the device comprises a lead cap configured to cover the proximal end of the lead.

In Example 3, the system according to Example 2, wherein the lead cap includes a connector block configured to electrically couple the lead cap with the connector on the lead to electrically terminate the lead.

In Example 4, the system according to any of Examples 1-3, wherein the device comprises a lead adapter.

In Example 5, the system according to Example 4, wherein the lead adapter further comprises a lead adapter connector configured to electrically couple with the connector on the lead, and wherein the lead adapter is configured to electrically and mechanically connect the lead to an implantable pulse generator.

In Example 6, the system according to either Example 4 or Example 5, wherein the lead adapter includes a connector block configured to electrically couple the lead adapter with the connector on the lead.

In Example 7, the system according to any of Examples 1-6, wherein the inductive element comprises a coil, and wherein a winding direction of the coil is same as a winding direction of the conductor.

In Example 8, the system according to any of Examples 1-7, wherein the conductor defines a lumen that extends through the lead, and wherein the system further comprises an inductive lumen coil positionable within the lumen proximate to the distal end of the conductor.

In Example 9, the system according to any of Examples 1-8, wherein the inductive element comprises one or more filars wound in a plurality of coil layers including a first coil layer of the one or more filars wound in a first winding direction, a second coil layer of the one or more filars coaxial with the first winding and wound in a second winding direction opposite the first winding direction, and a third coil layer of the one or more filars coaxial with the first and second windings and wound in the first winding direction.

In Example 10, a device for transforming a non-MR conditional lead into an MRI conditionally safe lead includes an insulative housing including a port configured to receive a connector of the non-MR conditional lead. The device further includes an inductive element disposed around at least a portion of the port and positioned within the housing such that the inductive element surrounds at least a portion of the connector from the non-MR conditional lead when the connector is received in the port.

In Example 11, the device according to Example 10, wherein the device is configured as a lead cap for covering the proximal end of the non-MR conditional lead.

In Example 12, the device according to either Example 10 or Example, 11, and further including a connector block configured to electrically couple the device with the connector on the lead such that the connector block electrically terminates the non-MR conditional lead.

In Example 13, the device according to any of Examples 10-12, wherein the device is configured as a lead adapter configured to electrically and mechanically connect the non-MR conditional lead to an implantable pulse generator, and wherein the device further comprises a lead adapter connector configured to electrically couple with the connector of the non-MR conditional lead.

In Example 14, the device according to Example 13, and further comprising a connector block configured to electrically couple the device with the connector on the non-MR conditional lead.

In Example 15, the device according to any of Examples 10-14, wherein the inductive element comprises a coil, and wherein a winding direction of the coil is the same as the winding direction of a conductor in the non-MR conditional lead.

In Example 16, the device according to any of Examples 10-15, wherein the inductive element comprises one or more filars wound in a plurality of coil layers, a first coil layer of the one or more filars wound in a first winding direction, a second coil layer of the one or more filars coaxial with the first winding and wound in a second winding direction opposite the first winding direction, and a third coil layer of the one or more filars coaxial with the first and second windings and wound in the first winding direction.

In Example 17, a lead assembly includes a non-MR conditional medical device lead including a connector at a proximal end of the lead, a conductor electrically connected to the connector at a proximal end of the conductor, and at least one electrode coupled to a distal end of the conductor. The lead assembly further comprises an inductive element secured to the proximal end of the lead and comprising a coil. The inductive element includes a port that receives the connector and positions the coil around at least a portion of the connector.

In Example 18, the lead assembly according to Example 17, wherein the device comprises a lead cap that covers the proximal end of the non-MR conditional medical device lead.

In Example 19, the lead assembly according to Example 17, wherein the device comprises a lead adapter, and wherein the lead adapter further comprises a lead adapter connector electrically coupled with the connector on the non-MR conditional medical device lead, and wherein the lead adapter is configured to electrically and mechanically connect the electrically coupled lead to an implantable pulse generator.

In Example 20, the lead assembly according to any of Examples 17-19, wherein the inductive element comprises a coil, and wherein a winding direction of the coil is the same as a winding direction of the conductor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
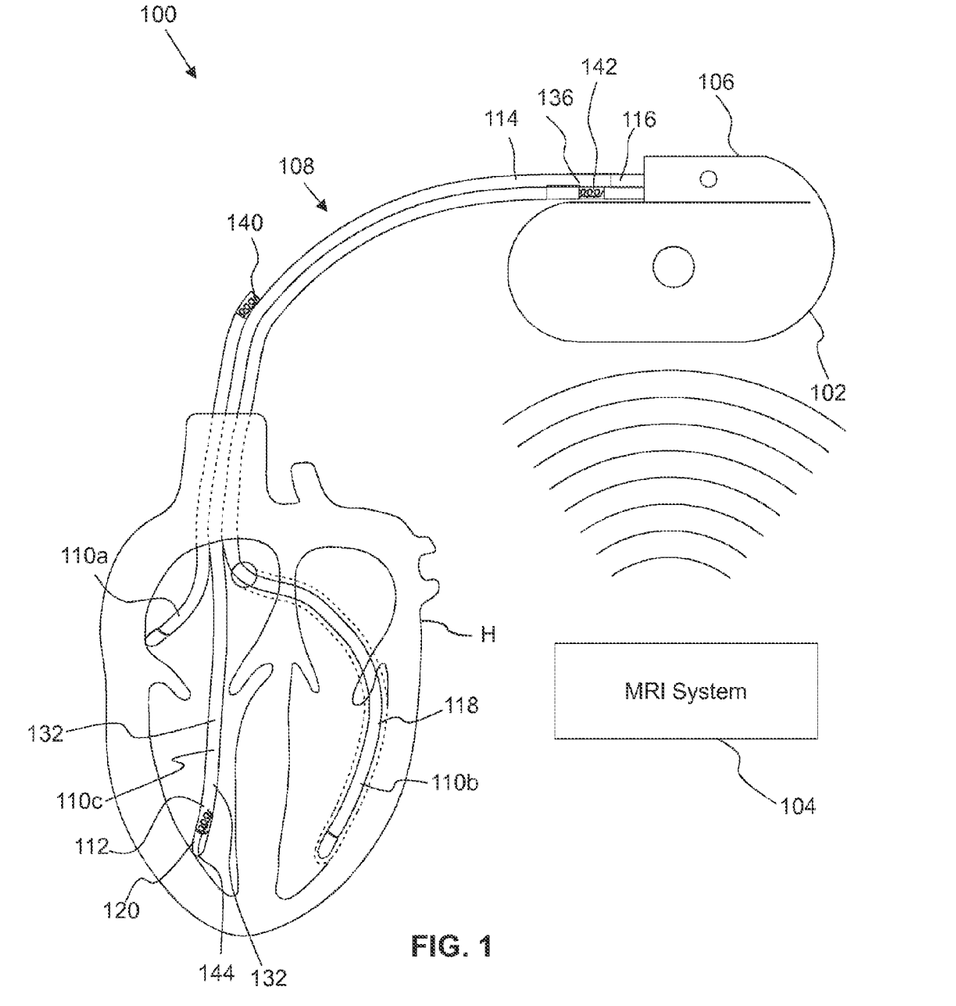
FIG. 1 is a schematic view of a system illustrating various embodiments of an inductive element for providing MRI compatibility in an implantable medical device lead.

FIG. 1 is a schematic view of a system 100 including an implantable medical device (IMD) 102. As is shown, the IMD 102 is disposed in the vicinity of a magnetic resonance imaging (MRI) system 104. The IMD 102 includes a pulse generator 106 and one or more leads 110 deployed in a patient's heart H. For purposes of illustration, FIG. 1 shows three leads, referred to as leads 110a, 110b, and 110c, implanted in various chambers of the heart H. The lead 110a is an abandoned lead, and the leads 110b and 110c are active leads coupled to the pulse generator 106.

The pulse generator 106 is typically implanted subcutaneously within an implantation location or pocket in the patient's chest or abdomen. The pulse generator 106 may be any implantable medical device, known in the art or later developed, for delivering an electrical therapeutic stimulus to the patient. In various embodiments, the pulse generator 106 is a pacemaker, an implantable cardiac defibrillator, and/or includes both pacing and defibrillation capabilities. Any excess lead length, i.e., length beyond that needed to reach from the location of the pulse generator 106 to the desired intracardiac implantation site, is generally coiled up in the subcutaneous pocket near the pulse generator 106.

Each of the leads 110a-110c includes a distal end 112 and a proximal end 114 (shown only on lead 110c for ease of illustration). Each of the leads 110a-110c includes a connector 116 at the proximal end 114. A conductor 118 extends through the lead body of each of the leads 110a-110c, and is coupled to the connector 116 at the proximal end 114 and to one or more electrodes 120 at the distal end 112. For ease of illustration, the connector 116, conductor 118, and electrode 120 are labeled only on lead 110c, but leads 110a and 110b can include similarly configured and located elements. It is noted that while one conductor 118 is shown, more than one conductor can be provided extending within each lead body.

In some embodiments, the conductor 118 is covered by an outer insulating layer that forms the lead body. In some embodiments, the conductor 118 defines a conductor lumen 132 that extends through the lead 110 (e.g., lead 110c) from the proximal end 114 to the distal end 112 of the lead 110.

The connector 116 couples each of the leads 110b and 110c to the pulse generator 106 to electrically connect the one or more electrodes 120 on the leads 110b, 110c to the pulse generator 106 via the conductor 118. As shown, the connector 116 of the lead 110a is configured for connection to the pulse generator 106, but is disconnected. A lead (e.g., lead 110a) that is not connected to a pulse generator 106 and subsequently left in the heart H is termed an "abandoned lead."

As shown in FIG. 1, the leads 110b and 110c operate to convey electrical signals and stimuli between the heart H and the pulse generator 106. For example, in the illustrated embodiment, the lead 110a is implanted in the right atrium, the lead 110b is implanted in the left ventricle, and the lead 110c is implanted into the right ventricle. As shown, the leads 110a-110c enter the vascular system through a vascular entry site formed in the wall of a left subclavian vein, extending through a brachiocephalic vein and a superior vena cava. In other embodiments, the leads 110a-110c may enter the vascular system through a right subclavian vein, a left axillary vein, a left external jugular, an internal jugular, or a left brachiocephalic vein. The electrical signals and stimuli conveyed by the pulse generator 106 are carried to the electrode 120 at the distal end 112 of the leads 110b, 110c by the conductor 118.

In an MRI environment, as shown in FIG. 1, the electromagnetic radiation produced by the MRI system 104 may be picked up by the conductor 118 of each of the leads 110a-110c, regardless of whether the leads 110a-110c are connected to the pulse generator 106. The electromagnetic energy is transferred through the leads 110a-110c to the electrode 120 in contact with the target tissue, which may lead to elevated temperatures at the point of contact.

The devices as described in further detail herein include inductive elements (e.g., inductive coils) and are configured to associate with non-MR conditional leads to transform the leads into MR conditional leads. An MR conditional device poses no known hazards in a specified MRI environment with specified conditions of use. In some embodiments, a device to transform a non-MR conditional lead into an MR conditional lead can include, for example, a lead cap 140 including an inductive element secured to the proximal end 114 of the lead, as shown attached to the lead 110a. An embodiment of the lead cap 140 according to the present disclosure is described below with regard to FIG. 2. A second example device to transform a non-MR conditional lead into an MR conditional lead can include a lead adapter 142 including an inductive element is secured to the proximal end 114 of the lead, as shown coupled to the proximal end of the lead 110b. An embodiment of the lead adapter 142 according to the present disclosure is described herein with regard to FIG. 3. A third example device can include an inductive coil 144 is positioned near the distal end 112 of the lead in the conductor lumen 132, as shown at the distal end of the lead 110c. An embodiment of the inductive coil 144 according to the present disclosure is described herein with regard to FIG. 4.

Figure 2:
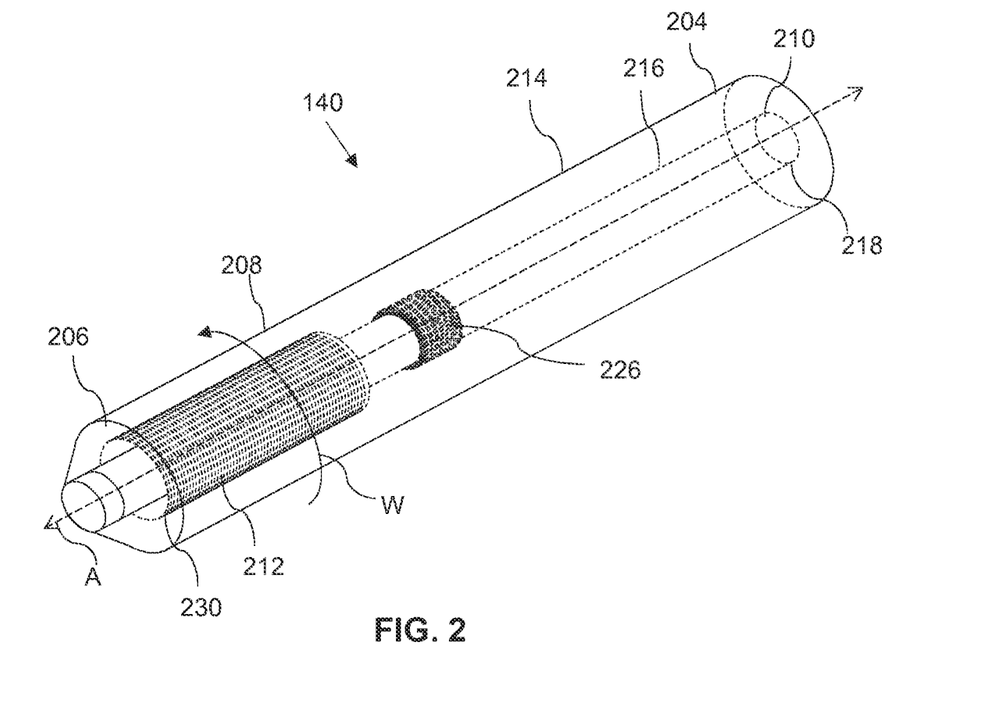
FIG. 2 is a schematic view of an embodiment of a lead cap including an inductive element.

FIG. 2 is a schematic illustration of a lead cap 140 configured to couple to the connector 116 at the proximal end 114 of the lead 110a (FIG. 1). The lead cap 140 has a distal end portion 204 and a proximal end portion 206. The lead cap 140 includes an insulative housing 208, a port 210, and an inductive element 212. The insulative housing 208 extends from the distal end portion 204 to the proximal end portion 206. The insulative housing 208 can include an outer wall 214 and an inner wall 216 and a lumen 218 defined within the inner wall 216 and extending from the proximal end portion 206 to the distal end portion 204 of the housing 208. The port 210 provides an opening to the lumen 218 at the distal end portion 204. The port 210 and lumen 218 are configured to receive and retain the connector 116. The inductive element 212 can be disposed around at least a portion of the port 210 and positioned within the housing 208 such that the inductive element 212 surrounds at least a portion of the connector 116 from the non-MR conditional lead when the connector is received in the lumen 218. In some embodiments, the inductive element 212 can be a high inductance coil.

In some embodiments, the housing 208 can be formed of a polymer. In some embodiments, the housing 208 is formed of a polymeric biocompatible material. Exemplary materials that may be used for the housing 208 is include, but are not limited to, expanded polytetrafluoroethylene (ePTFE), layered ePTFE, polytetrafluoroethylene (PTFE), polyethylene terephthalate (PETE), ethylene/tetrafluoroethylene copolymer (ETFE), fluorinated ethylene propylene (FEP), polyether ether ketone (PEEK), polyamides, polyimides, para-aramid synthetic fibers, and polyurethane, among other materials.

The lead cap 140 couples with the connector 116 of the lead 110a to electrically terminate the lead 110a. In some embodiments, such as in a unipolar lead, the lead cap 140 further includes a connector block 226. The connector block 226 can be electrically coupled to the inductive element 212. The connector block 226 is positioned around the lumen 218 within the housing 208 such that the connector block 226 is electrically connectable to a connector 116 disposed within the lumen 218. In some embodiments, the connector block 226 is mechanically and electrically couplable to the connector 116 using a fixation mechanism (not shown), such as one or more set screws. Thus, the connector block 226 operates to electrically couple the inductive element 212 to the connector 116. In other embodiments, the lead cap 140 may not include the connector block 226, which results in the inductive element 212 not being electrically connected to the connector 116. In such embodiments, the inductive element 212 "floats" over the connector 116.

In the illustrated embodiment, the inductive element 212 can include a single filar 230 that is helically wound with a plurality of turns around a longitudinal axis A of the lumen 218 in a particular winding direction W, for example, a left-handed (LH) winding direction. In some embodiments, the inductive element 212 can include two or more filars (see, e.g., FIG. 5). The inductive element 212 can also have a coil pitch, defined as a length from the center of a turn of a wire of the inductive element 212 to the center of an adjacent turn of the wire of the inductive element 212, of between about one and two times the diameter of the filar 230.

The inductance of the inductive element 212 can be determined, in part, by its geometric properties, including whether the inductive element 212 is straight or coiled. For a coiled or wound inductive element 212, several parameters influence its inductance, including the coil pitch, the outer diameter, the cross-sectional area of the inductive element 212, and the number of filars 230 in the inductive element 212. Thus, the dimensions and characteristics of the inductive element 212 may be selected to minimize the effects of MRI fields on the performance and response of the lead 110a.

In some embodiments, the inductive element 212 is wound in the same direction W as the conductor 118 in the lead 110a. For example, if the conductor 118 is coiled in the LH winding direction, then the inductive element 212 can also be coiled in the same LH winding direction. The inductive element 212 has a higher inductance than the conductor 118, so the overall inductance of the lead 110a is increased by coupling the inductive element 212 to the conductor 118. As a result, the amount of MRI induced current on the conductor 118 is reduced.

In operation, the lead cap 140 can be placed over the proximal end 114 of the lead 110a. The port 210 receives the connector 116 of the lead 110a, which traverses through the lumen 218 to the proximal end 206 of the lead cap 140 until the inductive element 212 is disposed around at least a portion of the connector 116. By surrounding at least a portion of the connector 116 with the inductive element 212, the overall inductance of the lead 110a is increased, thereby reducing the amount of MRI-induced current that is picked up and transmitted by the conductor 118. As a result, the inductive element 212 prevents or reduces temperature increase at the one or more electrodes 120.

Figure 3:
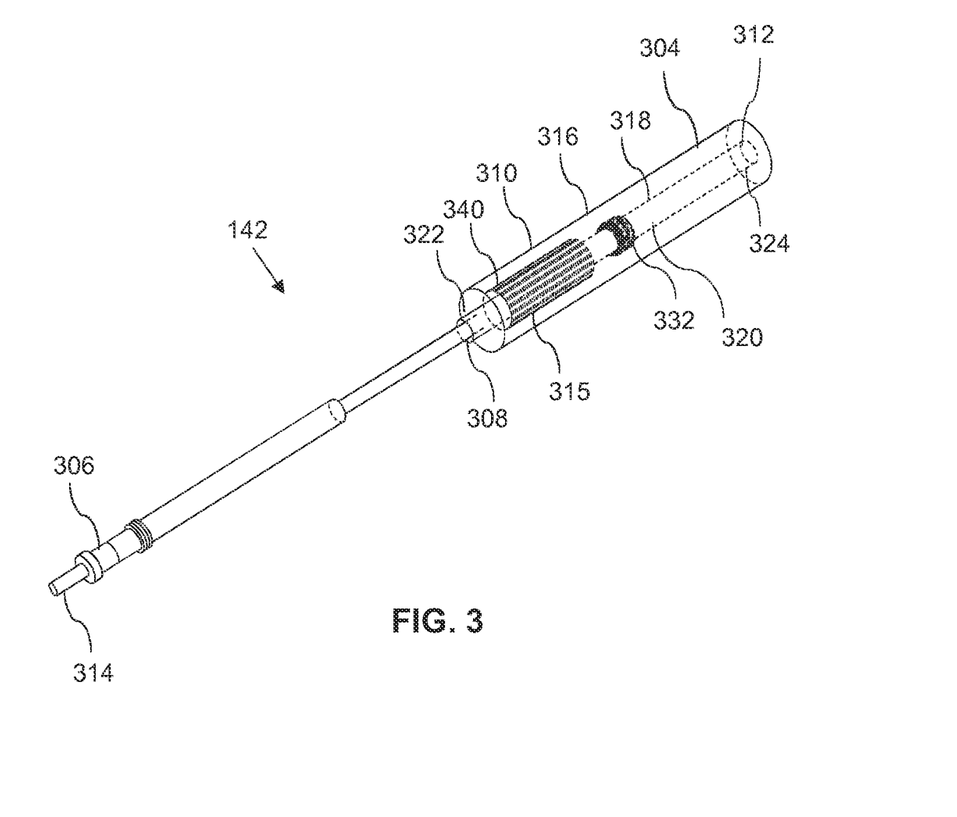
FIG. 3 is a schematic view of an embodiment of a lead adapter including an inductive element.

FIG. 3 is a schematic illustration of a lead adapter 142 configured to couple to and cover the connector 116 at the proximal end 114 of the lead 110b (FIG. 1). The lead adapter 142 has a distal end portion 304, a proximal end portion 306, and an intermediate portion 308. The lead adapter 142 can include an insulative housing 310, a port 312, a lead adapter connector 314, and an inductive element 315. The insulative housing 310 extends from the distal end portion 304 to the intermediate portion 308. The insulative housing 310 includes an outer wall 316, an inner wall 318, and a lumen 320 defined within the inner wall 318 and extending from a proximal end portion 322 to a distal end portion 324 of the housing 310. The port 312 provides an opening to the lumen 320 at the distal end portion 304 of the lead adapter 142. The port 312 and lumen 320 are configured to receive and retain the connector 116 on the lead 110b. The inductive element 315 can be disposed around at least a portion of the port 312 and positioned within the housing 310 such that the inductive element 315 surrounds at least a portion of the connector 116 from the non-MR conditional lead when the connector 116 is received in the lumen 320. In some embodiments, the inductive element 315 is a high inductance coil.

In some embodiments, the housing 310 can be formed of a polymer. In some embodiments, the housing 310 is formed of a polymeric biocompatible material. Exemplary materials that may be used for the housing 310 is include, but are not limited to, expanded ePTFE, layered ePTFE, PTFE, PETE, ETFE, FEP, PEEK, polyamides, polyimides, para-aramid synthetic fibers, polyurethane, and silicone, among others.

In some embodiments, such as when the lead adapter 142 is used in association with a unipolar lead, the lead adapter 142 can further include a connector block 332. The connector block 332 can be electrically coupled to the inductive element 315. The connector block 332 is positioned around the lumen 320 within the housing 310 such that the connector block 332 is electrically connectable to a connector 116 disposed within the lumen 320. In some embodiments, the connector block 332 is mechanically and electrically couplable to the connector 116 using a fixation mechanism (not shown), such as one or more set screws. Thus, the connector block 332 operates to electrically couple the inductive element 315 to the connector 116. In other embodiments, the lead adapter 142 may not include the connector block 332, which results in the inductive element 315 not being electrically connected to the connector 116. In such embodiments, the inductive element 315 "floats" over the connector 116.

In the illustrated embodiment, the inductive element 315 can include a single filar 340 that is helically wound with a plurality of turns around a longitudinal axis of the lumen 320 in a particular winding direction, for example, a left-handed (LH) winding direction. In other embodiments, the inductive element 315 includes two or more filars (see, e.g., FIG. 5). The inductive element 315 can also have a coil pitch of between about one and two times the diameter of the filar 340.

The inductance of the inductive element 315 is determined, in part, by its geometric properties, including whether the inductive element 315 is straight or coiled. For a coiled, or wound, inductive element 315 several parameters influence its inductance including: coil pitch, outer diameter, cross-sectional area of the inductive element 315, and number of filars 340 in the inductive element 315. Thus, the dimensions and characteristics of the inductive element 315 may be selected to minimize the effects of MRI fields on the performance and response of the lead 110b.

In some embodiments, the inductive element 315 can be wound in the same direction as the conductor 118 in the lead 110b. For example, if the conductor 118 is coiled in the LH winding direction, then the inductive element 315 can also be coiled in the same LH winding direction. The inductive element 315 can be configured to increase the overall inductance of the lead 110b to reduce the amount of MRI induced currents on the conductor 118.

In operation, the lead adapter 142 can be placed over the proximal end 114 of the lead 110b. The port 312 receives the connector 116 of the lead 110b, which traverses through the lumen 320 to the proximal end portion 322 of the housing 310 until the inductive element 315 is disposed around at least a portion of the connector 116. The lead adapter connector 314 is then coupled to the pulse generator 106. By surrounding at least a portion of the connector 116 with the inductive element 315, the overall inductance of the lead 110b is increased, thereby reducing the amount of MRI-induced current that is picked up and transmitted by the conductor 118. As a result, the inductive element 315 prevents or reduces temperature increase at the one or more electrodes 120, and can prevent or reduce the amount of current injected into the pulse generator 106.

Figure 4:
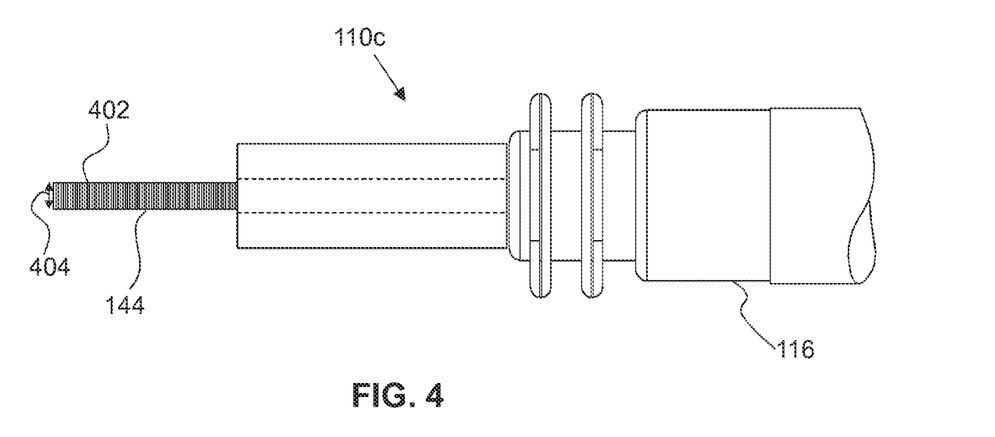
FIG. 4 is a schematic view of a proximal end of a lead illustrating an embodiment of an inductive coil insertable in an inner lumen of the lead.

FIG. 4 is a schematic illustration of a portion of the lead 110c with an embodiment of the inductive element 144 being inserted into the proximal end of the connector 116. As discussed herein, and illustrated in FIG. 1, the inductive element 144 can be configured to traverse through the conductor lumen 132 of the conductor 118 extending through the lead 110c. In some embodiments, the inductive element 144 is positioned at the distal end portion 112 of the lead 110c proximate to the one or more electrodes 120. The inductive element 144 increases the inductance of the conductor 118, thereby reducing the heating of the one or more electrodes at the distal end 112 of the lead 110c.

The inductive element 144 can be guided using an insertion tool (not shown) into the lumen 132 of the conductor 118 and moved toward the distal end portion 112 of the lead 110c proximate to the electrode 120. The insertion tool used can be a guide wire or a stylet. Other insertion tools can also be used for the purpose of guiding the inductive element 144 through the lead 110c. The inductive element 144 may be a high inductance coil and can include a wire or filar 402 wound into a coil with an outer diameter 404 smaller than the inner diameter of the conductor 118. The inductive element 144 can serve as a micro conductor for reducing the MRI field induced heating in the one or more electrodes 120. The inductive element 144 may be employed in lieu of or in addition to the lead cap 140 or the lead adapter 142 as discussed herein with respect to FIGS. 2 and 3, respectively.

Figure 5:
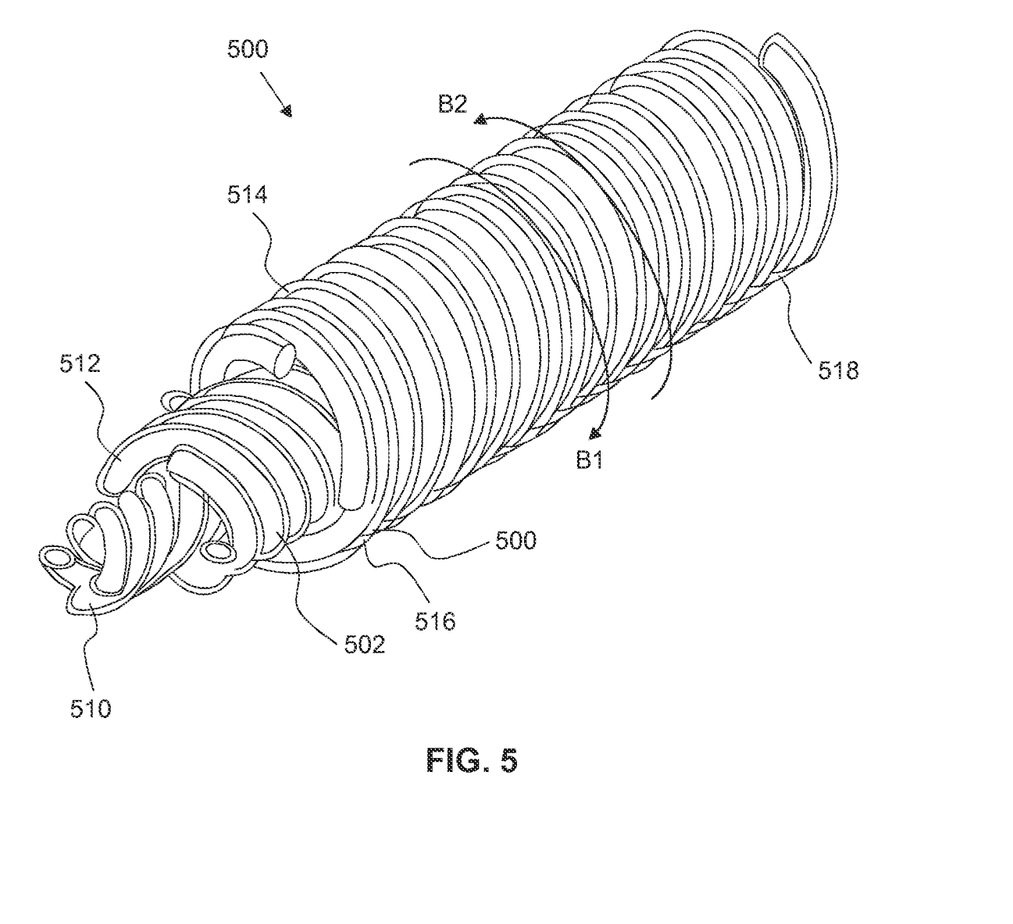
FIG. 5 is a perspective view of an embodiment of a high inductance coil according to embodiments of the present disclosure.

FIG. 5 is a perspective view of an inductive element 500, including one or more filars 502. The inductive element 500 is an alternative configuration to the coiled inductive elements as described herein with regard to FIGS. 2-4. In some embodiments, one or more filars 502 of the inductive element 500 are wound in a plurality of coil layers. For example, a first coil layer 510 can be wound in a first winding direction B1, a second coil layer 512 can be coaxial with the first winding and wound in a second winding direction B2 opposite the first winding direction, and a third coil layer 514 can be coaxial with the first and second windings and wound in the first winding direction B1. The inductive element 500 may be employed for the inductive elements described herein, including the inductive element 212 in the lead cap 140 (FIG. 2), the inductive element 315 in the lead adapter 142 (FIG. 3), and the inductive element 144 insertable in the conductor lumen 132 (FIG. 4).

In FIG. 5, portions of each of the plurality of coil layers have been removed to illustrate each of the underlying layers such as 510 and 512. The filars 502 of the inductive element 500 are co-radially wound along a direction for example, direction B1 to form the first coil layer 510 with a close pitch. The filars 502 are then wound back on themselves in the reverse direction over and coaxially with the first coil layer 510. The pitch of the second coil layer 512 may be greater than the pitch of the first coil layer 512, and winding in reverse direction results in the formation of second coil layer 512 over the first coil layer 510. The filars 502 are then wound back on themselves again, reversing direction from the second coil layer 512 (i.e., in the same direction as the inner first coil layer 510) to form the third coil layer 514 over the second coil layer 512. The pitch of the third coil layer 514 may be smaller than the pitch of the second coil layer 512.

In some embodiments, the inductive element 500 includes two to fifty filars 502. In some embodiments, the diameter of each filar 502 can be in the range of about 0.001 inch to 0.010 inch (0.003-0.025 cm). The filars may be composed of a biocompatible material, including, but not limited to, gold (Au), silver (Ag), Nitinol, titanium (Ti), platinum (Pt), iridium (Ir), a nickel-cobalt base alloy (MP35N), or stainless steel. Each of the filars may also include an insulation layer (not shown) of a biocompatible and dielectric material, such as, for example, Teflon, nylon, polymers, PTFE, ETFE, silicone, polyurethane, PEEK, and/or epoxy. The thickness of the insulation layer may be less than about 0.005 inch (0.01 cm). In some embodiments, the outside diameter of the conductive assembly is less than about 0.10 inch (0.25 cm).

Various modifications and additions can be made to the exemplary embodiments discussed without departing from the scope of the present invention. For example, while the embodiments described above refer to the particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

We claim:

1. A lead adapter configured to electrically and mechanically connect a lead to an implantable pulse generator, the lead having one or more electrodes and a connector, the lead adapter comprising:
   a port configured to receive the connector of the lead into a lumen of the lead adapter;
   a connector configured to be inserted into the pulse generator; and
   an inductive element, the inductive element entirely circumferentially surrounding at least a portion of the lumen such that the inductive element entirely circumferentially surrounds at least a portion of the connector of the lead when the connector of the lead is received within the lumen, wherein the inductive element does not directly electrically connect to any conductor of the lead when the connector of the lead is received within the lumen.

2. The lead adapter of claim 1, wherein the inductive element comprises a coil that surrounds the portion of the lumen.

3. The lead adapter of claim 2, wherein a winding direction of the coil is the same as a winding direction of a conductor of the lead.

4. The lead adapter of claim 1, wherein the inductive element comprises one or more filars wound in a plurality of coil layers, a first coil layer of the one or more filars wound in a first winding direction, a second coil layer of the one or more filars coaxial with the first winding and wound in a second winding direction opposite the first winding direction, and a third coil layer of the one or more filars coaxial with the first and second windings and wound in the first winding direction.

5. The lead adapter of claim 1, wherein the lead adapter comprises a proximal end portion, a distal end portion, and an intermediate portion between the proximal end portion and the distal end portion, wherein the port is located on the distal end portion and the connector of the lead adapter is located on the proximal end portion.

6. The lead adapter of claim 5, wherein the lead adapter further comprises an insulative housing that extends from the distal end portion to the intermediate portion.

7. The lead adapter of claim 6, wherein the insulative housing comprises an outer wall, an inner wall, and the lumen defined by the inner wall, the lumen extending from the proximal end portion to the distal end portion.

8. The lead adapter of claim 7, wherein the inductive element is located within the insulative housing.

9. The lead adapter of claim 1, wherein the port and the lumen are configured to retain the connector of the lead.

10. The lead adapter of claim 1, wherein in the lead is a non-MM conditional lead.

11. The system of claim 1, wherein the lead adapter includes a connector block configured to electrically couple the lead adapter with the connector on the lead.

12. A lead adapter configured to connect a lead to an implantable pulse generator, the lead having one or more electrodes and a connector, the lead adapter comprising:
    a distal end portion comprising a port that is configured to receive the connector of the lead;
    a proximal end portion comprising a connector that is configured to connect with the pulse generator; and
    an insulative housing having a lumen and an inductive element that entirely circumferentially surrounds at least a portion of the lumen, the lumen configured to receive at least a portion of the connector of the lead inserted through the port, the inductive element positioned such that the inductive element entirely circumferentially surrounds at least a portion of the connector of the lead when the connector of the lead is received within the lumen, wherein the inductive element does not directly electrically connect to the connector of the lead when the connector of the lead is received within the lumen.

13. The lead adapter of claim 12, wherein the inductive element comprises a coil that surrounds the portion of the lumen.

14. The lead adapter of claim 13, wherein a winding direction of the coil is the same as a winding direction of a conductor of the lead.

15. The lead adapter of claim 12, wherein the inductive element comprises one or more filars wound in a plurality of coil layers, a first coil layer of the one or more filars wound in a first winding direction, a second coil layer of the one or more filars coaxial with the first winding and wound in a second winding direction opposite the first winding direction, and a third coil layer of the one or more filars coaxial with the first and second windings and wound in the first winding direction.

16. The lead adapter of claim 12, wherein the insulative housing comprises an outer wall, an inner wall, and the lumen defined by the inner wall, the lumen extending from the proximal end portion to the distal end portion.

17. The lead adapter of claim 12, wherein the port and the lumen are configured to retain the connector of the lead.

18. The lead adapter of claim 12, wherein in the lead is a non-MRI conditional lead.

19. The system of claim 12, wherein the lead adapter includes a connector block configured to electrically couple the lead adapter with the connector on the lead.

20. A lead adapter configured to electrically and mechanically connect a lead to an implantable pulse generator, the lead having one or more electrodes and a connector, the lead adapter comprising:
- a port configured to receive the connector of the lead into a lumen of the lead adapter;
- a connector configured to be inserted into the pulse generator; and
- an inductive coil, the inductive coil entirely circumferentially surrounding at least a portion of the lumen such that the inductive coil entirely circumferentially surrounds at least a portion of the connector of the lead when the connector of the lead is received within the lumen, wherein the inductive coil does not directly electrically connect to the connector of the lead when the connector of the lead is received within the lumen.

* * * * *